(12) United States Patent
Neal

(10) Patent No.: US 9,810,668 B2
(45) Date of Patent: Nov. 7, 2017

(54) AUTOSAMPLER AND GAS CHROMATOGRAPHY SYSTEM AND METHOD INCLUDING SAME

(71) Applicant: PerkinElmer Health Sciences, Inc., Waltham, MA (US)

(72) Inventor: Timothy Neal, Harwinton, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 274 days.

(21) Appl. No.: 14/626,222

(22) Filed: Feb. 19, 2015

(65) Prior Publication Data
US 2016/0245730 A1    Aug. 25, 2016

(51) Int. Cl.
G01N 1/24 (2006.01)
G01N 30/24 (2006.01)
G01N 35/02 (2006.01)
G01N 35/10 (2006.01)
G01N 35/04 (2006.01)

(52) U.S. Cl.
CPC .......... G01N 30/24 (2013.01); G01N 35/025 (2013.01); G01N 35/1011 (2013.01); G01N 35/1079 (2013.01); G01N 35/1095 (2013.01); G01N 2035/0441 (2013.01)

(58) Field of Classification Search
CPC .. G01N 30/24; G01N 35/025; G01N 35/1011; G01N 35/1079; G01N 35/1095; G01N 2035/0441
USPC ........................................................ 73/23.41
See application file for complete search history.

(56) References Cited

U.S. PATENT DOCUMENTS

| 4,713,974 | A | * | 12/1987 | Stone ..................... G01N 30/24 422/64 |
| 5,301,261 | A | * | 4/1994 | Poole ..................... G01N 30/24 210/360.1 |
| 5,601,707 | A | * | 2/1997 | Clay .................. B01D 11/0203 210/198.2 |

(Continued)

OTHER PUBLICATIONS

Agilent 7673 Automatic Liquid Sampler Operating Manual G1513-90107 First Edition May 2000.*

(Continued)

Primary Examiner — Natalie Huls
Assistant Examiner — Monica S Young
(74) Attorney, Agent, or Firm — Myers Bigel, P.A.

(57) ABSTRACT

A gas chromatography system includes at least one gas chromatography subsystem including at least one injector port, and an autosampler. The autosampler includes a carousel tray mounted for rotation about a rotation axis and including arcuately extending first and second rows of sample reservoirs, a first sample transfer tower to extract samples from the first row, a second sample transfer tower to extract samples from the second row, and a control system operative to: selectively position the carousel tray relative to the first and second sample transfer towers to align the first and second sample transfer towers with a selected pair of the sample reservoirs of the first and second rows, respectively; draw samples from the selected pair using the first and second sample transfer towers; inject the sample drawn from the first row into the at least one injector port using the first sample transfer tower; and inject the sample drawn from the second row into the at least one injector port using the second sample transfer tower.

18 Claims, 11 Drawing Sheets

(56) References Cited

U.S. PATENT DOCUMENTS

| | | |
|---|---|---|
| 5,686,656 A | 11/1997 | Amirav et al. |
| 5,711,786 A | 1/1998 | Hinshaw |
| 6,652,625 B1 | 11/2003 | Tipler et al. |
| 7,178,414 B1 * | 2/2007 | Kokosa ............ G01N 30/24 73/863.32 |
| 8,695,444 B2 | 4/2014 | Hiltbrand |
| 2013/0139568 A1 | 6/2013 | Guieze et al. |
| 2014/0030818 A1 | 1/2014 | Schueler et al. |

OTHER PUBLICATIONS

"PAL GC-xt Prep and Load Platform", LEAP Technologies, Inc., Jan. 1, 2010, 8 pages.

* cited by examiner

US 9,810,668 B2

AUTOSAMPLER AND GAS CHROMATOGRAPHY SYSTEM AND METHOD INCLUDING SAME

FIELD

The present technology relates to gas chromatography and, more particularly, to autosamplers for gas chromatography systems.

BACKGROUND

Gas chromatography is commonly used in analytic chemistry for separating and analyzing compounds of a sample. For example, a gas chromatograph may be used to test the purity of a sample, identify a compound, separate different components of a mixture or to prepare (e.g., purify) compounds from a mixture. Gas chromatography is essentially a physical method of separation in which constituents of a test sample in a carrier gas are adsorbed and desorbed by a stationary phase material in a column. A pulse of the sample is injected into a steady flow of carrier gas. At the end of the column the individual components are more or less separated in time. Detection of the gas provides a time-scaled pattern which, by calibration or comparison with known samples, indicates the constituents of the test sample. The main components of such a system are the column, an injector for introducing the sample into carrier gas and passing the mixture into the column, a device for transferring sample into the injector, a detector at the outer end of the column, gas controls, and a device such as a computer for treating and displaying the output of the detector. An oven may be used to elevate temperature to maintain the sample in a volatile state, and to improve the discrimination of constituents.

SUMMARY

According to embodiments of the technology, a gas chromatography system includes at least one gas chromatography subsystem including at least one injector port, and an autosampler. The autosampler includes a carousel tray mounted for rotation about a rotation axis. The carousel tray includes an arcuately extending first row of sample reservoirs and an arcuately extending second row of sample reservoirs. The autosampler further includes a first sample transfer tower to extract samples from the first row of sample reservoirs and a second sample transfer tower to extract samples from the second row of sample reservoirs. The autosampler further includes a control system operative to: selectively position the carousel tray relative to the first and second sample transfer towers to align the first and second sample transfer towers with a selected pair of the sample reservoirs of the first and second rows, respectively; draw samples from the selected pair of the sample reservoirs using the first and second sample transfer towers; inject the sample drawn from the first row into the at least one injector port using the first sample transfer tower; and inject the sample drawn from the second row into the at least one injector port using the second sample transfer tower.

In some embodiments, the gas chromatography system includes first and second gas chromatography subsystems each including: a sample injector; a column fluidly connected to the sample injector; and a detector fluidly connected to the column. The sample injector of the first gas chromatography subsystem includes a first injector port and the sample injector of the second gas chromatography subsystem includes a second injector port. The control system is operative to: inject the sample drawn from the first row into the first injector port using the first sample transfer tower; and inject the sample drawn from the second row into the second injector port using the second sample transfer tower. According to some embodiments, the control system is operative to substantially simultaneously draw the samples from the selected pair of the sample reservoirs using the first and second sample transfer towers. According to some embodiments, the control system is operative to substantially simultaneously inject the samples drawn from the first and second rows into the first and second injector ports using the first and second sample transfer towers. In some embodiments, the control system is operative to: selectively reposition the carousel tray relative to the first and second sample transfer towers to align the first and second sample transfer towers with a selected second pair of the sample reservoirs of the first and second rows, respectively; draw further samples from the selected second pair of the sample reservoirs using the first and second sample transfer towers; inject the further sample drawn from the first row into the at least one injector port using the first sample transfer tower; and inject the further sample drawn from the second row into the at least one injector port using the second sample transfer tower.

According to some embodiments, the first and second sample transfer towers are fixed in alignment with the first and second injector ports, respectively.

In some embodiments, each of the first and second sample transfer towers includes a syringe including a needle and a syringe actuator, and the control system is operative to: drive the needles of the first and second sample transfer towers into the selected sample reservoirs and to operate the syringes using the associated syringe actuators to draw the samples therefrom; and drive the needles of the first and second sample transfer towers into the first and second injector ports and to operate the syringes using the associated syringe actuators to inject the samples into the first and second injector ports.

According to some embodiments, the second row is located radially between the first row and the rotation axis of the carousel tray, According to method embodiments of the technology, a method for performing gas chromatography includes providing a gas chromatography system including at least one gas chromatography subsystem including at least one injector port, and an autosampler. The autosampler includes a carousel tray mounted for rotation about a rotation axis. The carousel tray includes an arcuately extending first row of sample reservoirs, and an arcuately extending second row of sample reservoirs. The autosampler further includes: a first sample transfer tower to extract samples from the first row of sample reservoirs; a second sample transfer tower to extract samples from the second row of sample reservoirs; and a control system. The method further includes: selectively positioning the carousel tray relative to the first and second sample transfer towers to align the first and second sample transfer towers with a selected pair of the sample reservoirs of the first and second rows, respectively; drawing samples from the selected pair of the sample reservoirs using the first and second sample transfer towers; injecting the sample drawn from the first row into the at least one injector port using the first sample transfer tower; and injecting the sample drawn from the second row into the at least one injector port using the second sample transfer tower.

According to some embodiments, the gas chromatography system includes first and second gas chromatography subsystems each including: a sample injector; a column fluidly connected to the sample injector; and a detector fluidly connected to the column; wherein the sample injector of the first gas chromatography subsystem includes a first injector port and the sample injector of the second gas chromatography subsystem includes a second injector port. The method further includes: injecting the sample drawn from the first row into the first injector port using the first sample transfer tower; and injecting the sample drawn from the second row into the second injector port using the second sample transfer tower. In some embodiments, the method includes substantially simultaneously drawing the samples from the selected pair of the sample reservoirs using the first and second sample transfer towers. In some embodiments, the method included substantially simultaneously injecting the samples drawn from the first and second rows into the first and second injector ports using the first and second sample transfer towers. In some embodiments, the method includes: selectively repositioning the carousel tray relative to the first and second sample transfer towers to align the first and second sample transfer towers with a selected second pair of the sample reservoirs of the first and second rows, respectively; drawing further samples from the selected second pair of the sample reservoirs using the first and second sample transfer towers; injecting the further sample drawn from the first row into the at least one injector port using the first sample transfer tower; and injecting the further sample drawn from the second row into the at least one injector port using the second sample transfer tower.

According to some embodiments, the first and second sample transfer towers are fixed in alignment with the first and second injector ports, respectively, throughout the steps of: drawing samples from the selected pair of the sample reservoirs using the first and second sample transfer towers; injecting the sample drawn from the first row into the at least one injector port using the first sample transfer tower; and injecting the sample drawn from the second row into the at least one injector port using the second sample transfer tower.

According to some embodiments, each of the first and second sample transfer towers includes a syringe including a needle and a syringe actuator, and the method includes: driving the needles of the first and second sample transfer towers into the selected sample reservoirs and operating the syringes using the associated syringe actuators to draw the samples therefrom; and driving the needles of the first and second sample transfer towers into the first and second injector ports and operating the syringes using the associated syringe actuators to inject the samples into the first and second injector ports.

In some embodiments, the second row is located radially between the first row and the rotation axis of the carousel tray.

According to embodiments of the technology, an autosampler for a gas chromatography system includes a carousel tray mounted for rotation about a rotation axis. The carousel tray includes an arcuately extending first row of sample reservoirs and an arcuately extending second row of sample reservoirs. The autosampler further includes a first sample transfer tower to extract samples from the first row of sample reservoirs, a second sample transfer tower to extract samples from the second row of sample reservoirs, and a control system. The control system is operative to: selectively position the carousel tray relative to the first and second sample transfer towers to align the first and second sample transfer towers with a selected pair of the sample reservoirs of the first and second rows, respectively; and draw samples from the selected pair of the sample reservoirs using the first and second sample transfer towers.

In some embodiments, the control system is operative to substantially simultaneously draw the samples from the selected pair of the sample reservoirs using the first and second sample transfer towers.

According to some embodiments, the control system is operative to: inject the sample drawn from the first row into a first injector port of the gas chromatograph using the first sample transfer tower; and inject the sample drawn from the second row into a second injector port of the gas chromatograph using the second sample transfer tower. In some embodiments, the control system is operative to substantially simultaneously inject the samples drawn from the first and second rows into the first and second injector ports using the first and second sample transfer towers.

Further features, advantages and details of the present technology will be appreciated by those of ordinary skill in the art from a reading of the figures and the detailed description of the preferred embodiments that follow, such description being merely illustrative of the present technology.

DETAILED DESCRIPTION

Figure 1:
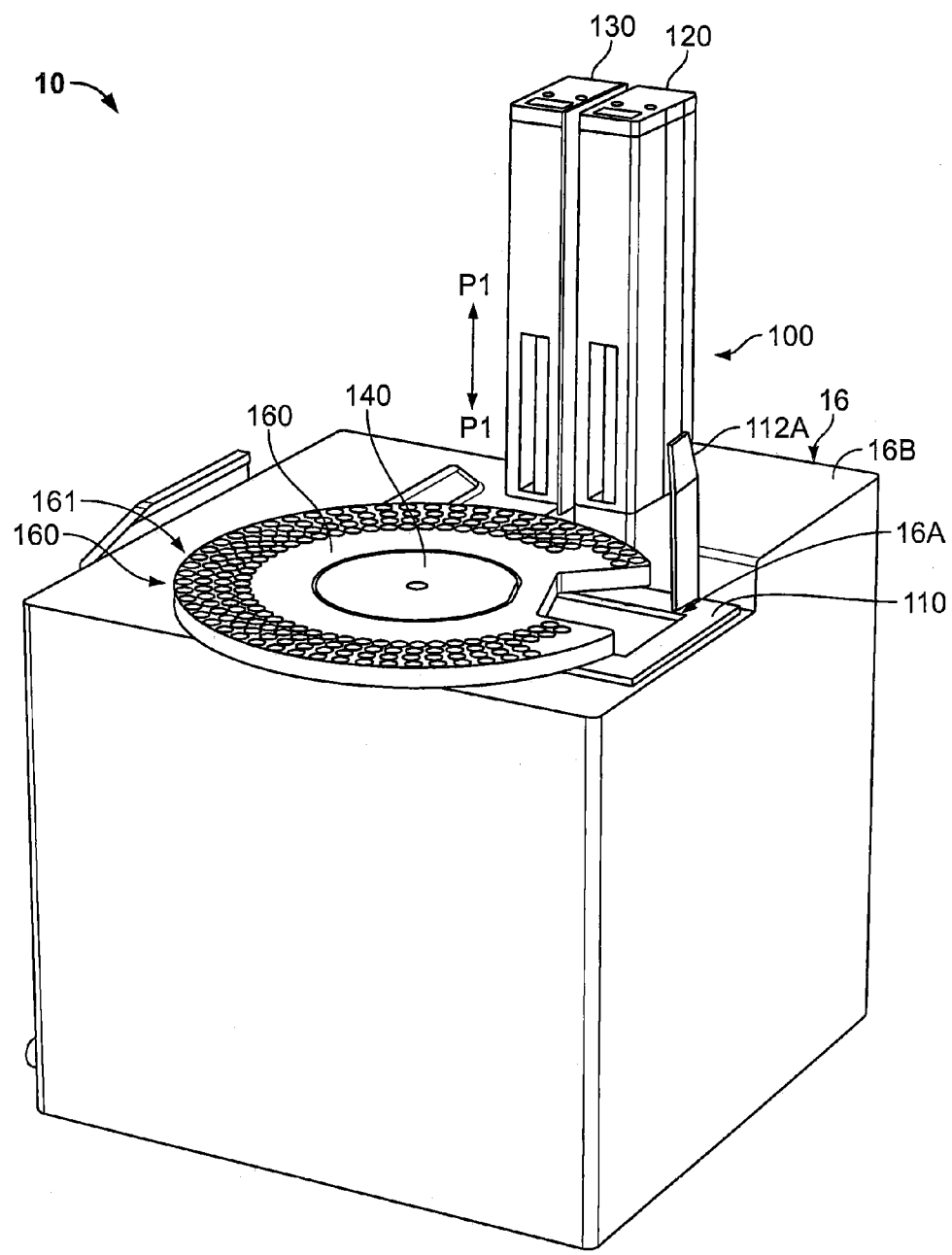
FIG. 1 is a perspective view of a gas chromatography (GC) system including an autosampler according to embodiments of the technology.
Figure 2:
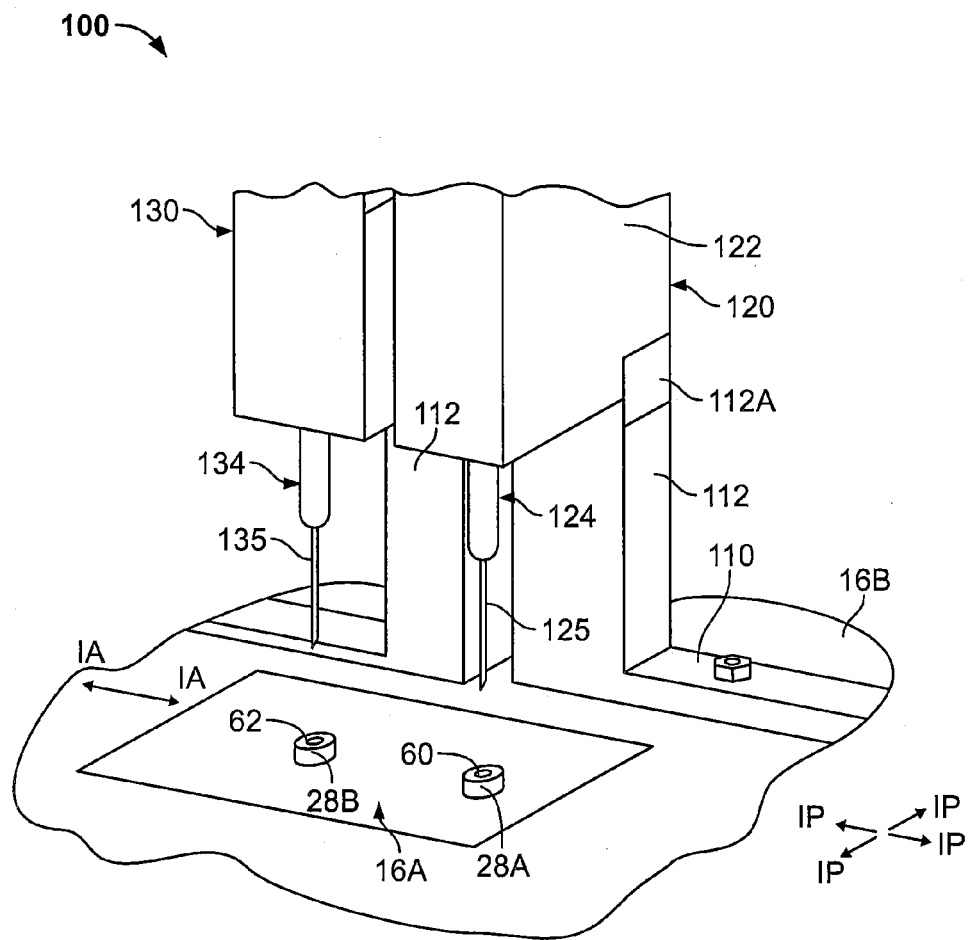
FIG. 2 is an enlarged, fragmentary, perspective view of the GC system of FIG. 1.
Figure 3:
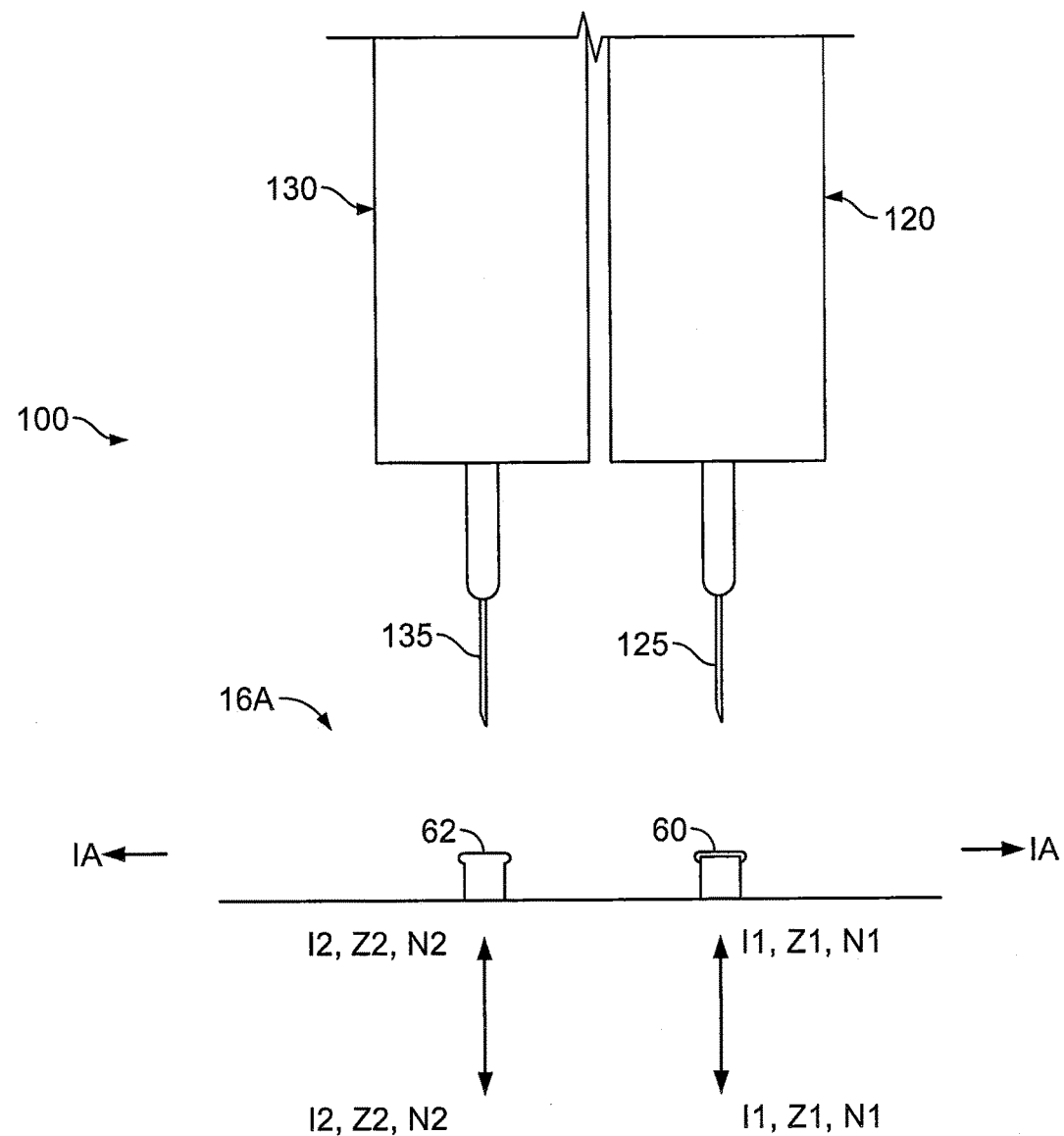
FIG. 3 is an enlarged, fragmentary, front elevational view of the GC system of FIG. 1.

The present technology now will be described more fully hereinafter with reference to the accompanying drawings, in which illustrative embodiments of the technology are shown. In the drawings, the relative sizes of regions or features may be exaggerated for clarity. This technology may, however, be embodied in many different forms and should not be construed as limited to the embodiments set forth herein; rather, these embodiments are provided so that this disclosure will be thorough and complete, and will fully convey the scope of the technology to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present technology.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

The term "automatically" means that the operation is substantially, and may be entirely, carried out without human or manual input, and can be programmatically directed or carried out.

The term "programmatically" refers to operations directed and/or primarily carried out electronically by computer program modules, code and/or instructions.

The term "electronically" includes both wireless and wired connections between components.

With reference to the figures, a gas chromatography (GC) system 10 (FIGS. 1-11) according to some embodiments of the technology is schematically shown therein. The GC system 10 is shown schematically in FIG. 10. The GC system 10 includes an autosampler 100 according to embodiments of the technology and as described in more detail herein below. The autosampler 100 includes a carousel tray 160, a first sample transfer unit or tower 120 and a second sample transfer unit or tower 130. The carousel tray 160 supports a plurality of sample supplies 5.

Figure 10:
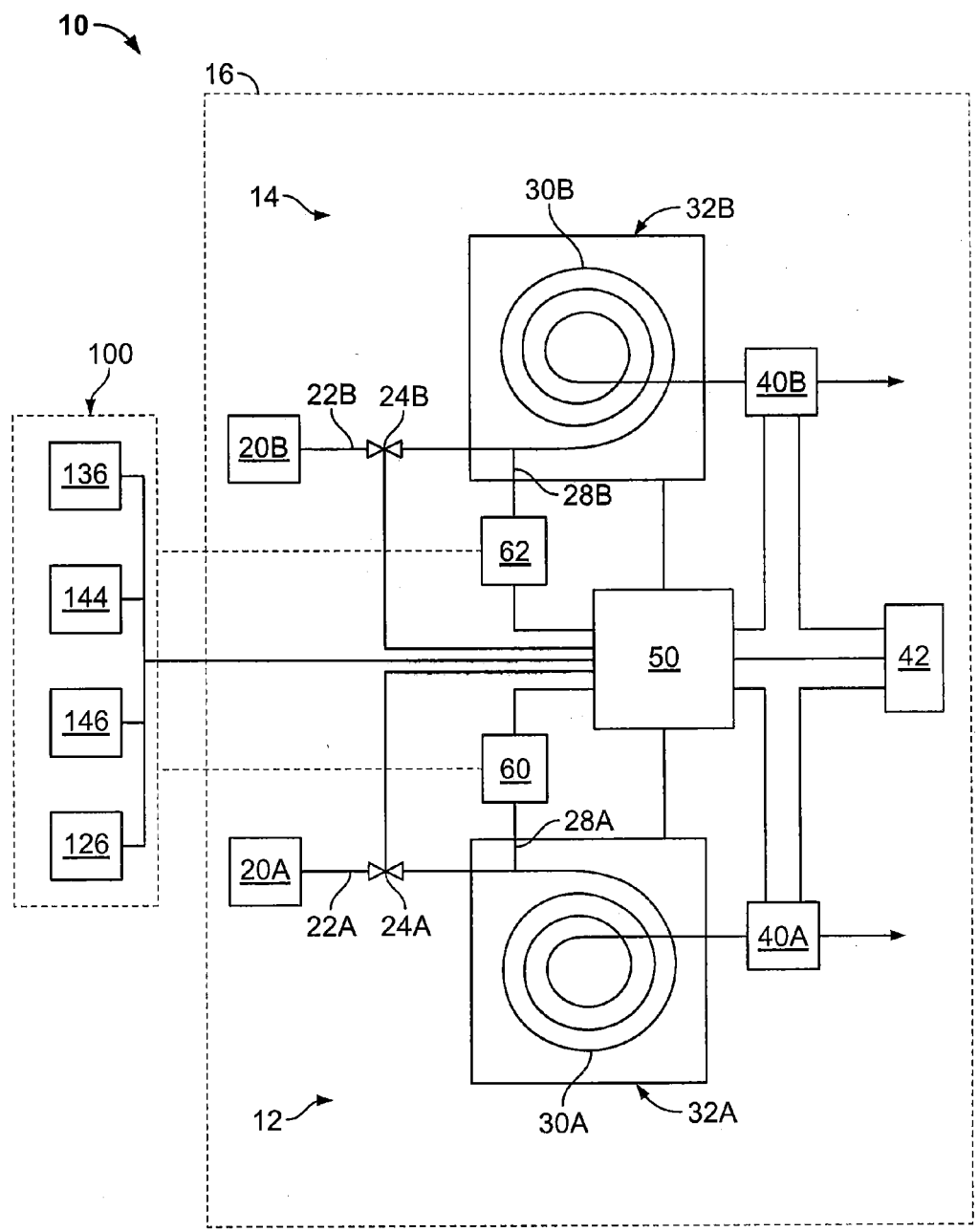
FIG. 10 is as schematic diagram of the GC system of FIG. 1.

With reference to FIGS. 1 and 10 the GC system 10 further includes a frame, cabinet or enclosure 16, a controller 50, a recorder 42, a first GC subsystem 12 and a second GC subsystem 14 mounted in or on the cabinet 16. The first GC subsystem 12 includes a carrier gas supply 20A, a feed line 22A, a flow controller or regulator 24A in the feed line 22A, a column inlet or sample injector 28A (including an injector inlet port 60), a column tubing 30, a GC oven 32A, and a detector 40. The second GC subsystem 14 includes a carrier gas supply 20B, a feed line 22B, a flow controller or regulator 24B in the feed line 22B, a column inlet or sample injector 28B (including an injector inlet port 62), a column tubing 30B, a GC oven 32B, and a detector 40B. The various components and architecture of the GC system 10 may be modified as desired and an autosampler 100 as disclosed herein may be incorporated into any suitable GC system.

Exemplary operation of the GC system 10 will now be described with the exception of the more particular operation of the autosampler 100. Referring to operation of the GC subsystem 12, the carrier gas supply 20A provides a continuous, pressurized flow of a selected carrier gas (the mobile phase) via the feed line 22A to an inlet of the column 30A. The flow rate of the supplied carrier gas can be controlled using the flow controller 24A. A first transfer unit 120 of the autosampler 100 transfers a sample into the sample injector 28A through the injector port 60. The sample injector 28A in turn introduces the sample into the continuous flow of the carrier gas. The carrier gas sweeps the sample through the column 30A to the detector 40A, and thereafter to waste collection, a further detector or other desired destination. The oven 32A selectively heats the column 30A before, during and/or after the sample is passed therethrough in order to control the temperature of the column 30A and the sample. The column 30A includes an inner layer or packing of a selected stationary phase in or on the inner wall of the bore of the column 30A. The gaseous compounds of the sample interact with the stationary phase which, having a different affinity for each component, retains the different components of the sample for different times. As a result, the different compounds elute at different times and take different amounts of time to pass through and exit the column 30A to the detector 40A (i.e., the components have different retention times within the column 30A). The detector 40A monitors the outlet stream from the column 30A to detect or sense the time at which each analyte component emerges from the column 30A and reaches the detector 40A, and/or the amount of the analyte. The detection data from the detector 40A is stored by the recorder 42. Various parameters of the process may be controlled by the controller 50, including the carrier gas flow rate (using the flow controller 24A), the column and/or mobile phase temperatures (using the GC oven 32A), and the sample injection timing and rate (using the sample injector 28A and the autosampler 100).

Referring to operation of the GC subsystem 14, the carrier gas supply 20B provides a continuous, pressurized flow of a selected carrier gas (the mobile phase) via the feed line 22B to an inlet of the column 30B. The flow rate of the supplied carrier gas can be controlled using the flow controller 24B. A second transfer unit 130 of the autosampler 100 transfers a sample into the sample injector 28B through the injector port 62. The sample injector 28B in turn introduces the sample into the continuous flow of the carrier gas. The carrier gas sweeps the sample through the column 30B to the detector 40B, and thereafter to waste collection, a further detector or other desired destination. The oven 32B selectively heats the column 30B before, during and/or after the sample is passed therethrough in order to control the temperature of the column 30B and the sample. The column 30B includes an inner layer or packing of a selected stationary phase in or on the inner wall of the bore of the column 30B. The gaseous compounds of the sample interact with the stationary phase which, having a different affinity for each component, retains the different components of the sample for different times. As a result, the different compounds elute at different times and take different amounts of time to pass through and exit the column 30B to the detector 40B (i.e., the components have different retention times within the column 30B). The detector 40B monitors the outlet stream from the column 30B to detect or sense the time at which each analyte component emerges from the column 30B and reaches the detector 40B, and/or the amount of the analyte. The detection data from the detector 40B is stored by the recorder 42. Various parameters of the process may be controlled by the controller 50, including the carrier gas flow rate (using the flow controller 24B), the column and/or mobile phase temperatures (using the GC oven 32B), and the sample injection timing and rate (using the sample injector 28B and the autosampler 100).

The GC subsystems 12, 14 may be operated independently or simultaneously. In some cases, it may be desirable to substantially simultaneously inject a first sample into the injector port 60 and a second sample into the injector port 62.

According to some embodiments, the GC ovens 32A, 32B heat or cool the column 30A, 30B to a temperature in the range of from about 100° C. to 450° C., The carrier gas may be any suitable gas. The carrier gas may include helium, nitrogen, hydrogen or argon, for example.

The columns 30A, 30B may be wound or coiled into a coil. The columns 30A, 30B may be formed of any suitable material. In some embodiments, the columns 30A, 30B are formed of fused silica or other glass. In some embodiments, the columns 30A, 30B are formed of metal. In some embodiments, the columns 30A, 30B are capillary tubing (e.g., glass capillary tubing). In some embodiments, the columns 30A, 30B are packed or coated in its interior bore with the stationary phase. According to some embodiments, the columns 30A, 30B have a bore inner diameter in the range of from about 50 μm to 1500 μm and, in some embodiments, from about 250 μm to 530 μm.

The detectors 40A, 40B may be any suitable detectors. Multiple detectors may be provided to monitor the gas stream. Suitable detectors may include, for example, a flame ionization detector (FID), a thermal conductivity detector (TCD), an electron capture detector (ECD), a nitrogen-phosphorous detector (NPD), a flame photometric detector (FPD), a photoionization detector (PID) and a mass spectrometer (MS).

The controller 50 may be any suitable device for providing the functionality described herein. According to some embodiments, the controller 50 is a microprocessor-based computer.

The injector ports 60, 62 (FIGS. 2 and 3) are located in fixed relative positions in an injector region 16A on a deck 16B of the cabinet 16. The first injector port 60 has a vertical first injector port axis I1-I1. The second injector port 62 has a vertical second injector port axis I2-I2. A common injector port pair axis IA-IA intersects the axes I1-I1 and I2-I2 and lies in an injector port plane IP-IP that is orthogonal to the axes I1-I1, I2-I2.

The autosampler 100 includes a support frame 110, a first or front sample transfer unit or tower 120 (hereinafter, the first tower 120), a second or rear sample transfer unit or tower 130 (hereinafter, the second tower 130), a carousel carrier 140, a support arm 142, a carousel sample tray 160, a rotation actuator 144, and a lateral position actuator 146. For the purpose of description, the reference X-axis extends front-rear, the reference Y-axis extends left-right, and the Z-axis extends top-bottom.

The support frame 110 is secured to the cabinet 16 (e.g., by bolts). The support frame 110 defines an opening and has two upstanding posts 112. The towers 120, 130 are each mounted on a respective one of the posts and thereby affixed to the cabinet 16. In some embodiments, the support frame 110 is removably and replaceably secured to the cabinet 16. In some embodiments, mechanisms or features are provided to enable adjustment of the alignment between the towers 120, 130 and the injector ports 60, 62. In some embodiments, hinge mechanisms 112A are provided on the posts 112 to enable the towers 120, 130 to be pivoted away from the injector ports 60, 62. In some embodiments, the towers 120, 130 are removable from the posts 112 to permit access to the injector ports 60, 62. The support frame 110 may be formed of any suitable material such as steel.

The first tower 120 includes a housing 122, a syringe 124, a syringe actuator 126, and a linkage mechanism. The syringe 124 includes a barrel 124A, a plunger 124B, and a needle 125 having a distal tip 125A. The syringe 124 is mounted in the housing 122 such that it can extend through a lower opening 122A in the housing 122. More particularly, the needle 125 can be moved (translated) and reciprocated in an upward direction E and a downward direction F along a displacement axis Z1-Z1 (FIGS. 3 and 4) coincident with the lengthwise axis N1-N1 of the needle 125. This movement is effected by the actuator 126 (e.g., under the control of the controller 50) through the linkage mechanism. The actuator 126 and the linkage mechanism also serve to forcibly displace the plunger 124B into and out from the barrel 124A. It will be appreciated that other configurations of actuators, linkages and sample handling devices (e.g., syringes) may be employed.

The tower 130 includes a housing 132, a syringe 134, a syringe actuator 136, and a linkage mechanism (not labeled) corresponding to the housing 122, the syringe 124, the syringe actuator 126, and the linkage mechanism 128, respectively. The actuator 136 and its associated linkage are likewise operable to move (translate) and reciprocate the needle 135 in an upward direction E and a downward direction F along a displacement axis Z2-Z2 (FIGS. 2 and 4) coincident with the lengthwise axis N2-N2 of the needle 135.

The first needle axis N1-N1 and displacement axis Z1-Z1 are each aligned or coaxial with the first injector port axis I1-I1. The second needle axis N2-N2 and displacement axis Z2-Z2 are each aligned or coaxial with the second injector port axis I2-I2. In use and as discussed below, the towers 120, 130 and syringes 124, 134 are stationarily mounted or fixed with respect to the injector ports 60, 62 so that these coaxial relationships are maintained throughout the autosampling procedure (i.e., sample extraction and dispensing into the injector ports).

The carousel tray 160 (FIG. 6) includes a body 162, a mount opening 162A, a surrounding peripheral edge 164, and a sample slot array 169. An array 179 of sample containers or vials 170 are mounted in the sample slot array 169 and the tray 160 and the vials 170 collectively form a carousel tray assembly 161.

The peripheral edge 164 defines a radially inwardly extending, sidewardly opening side opening or slot 166.

Figure 4:
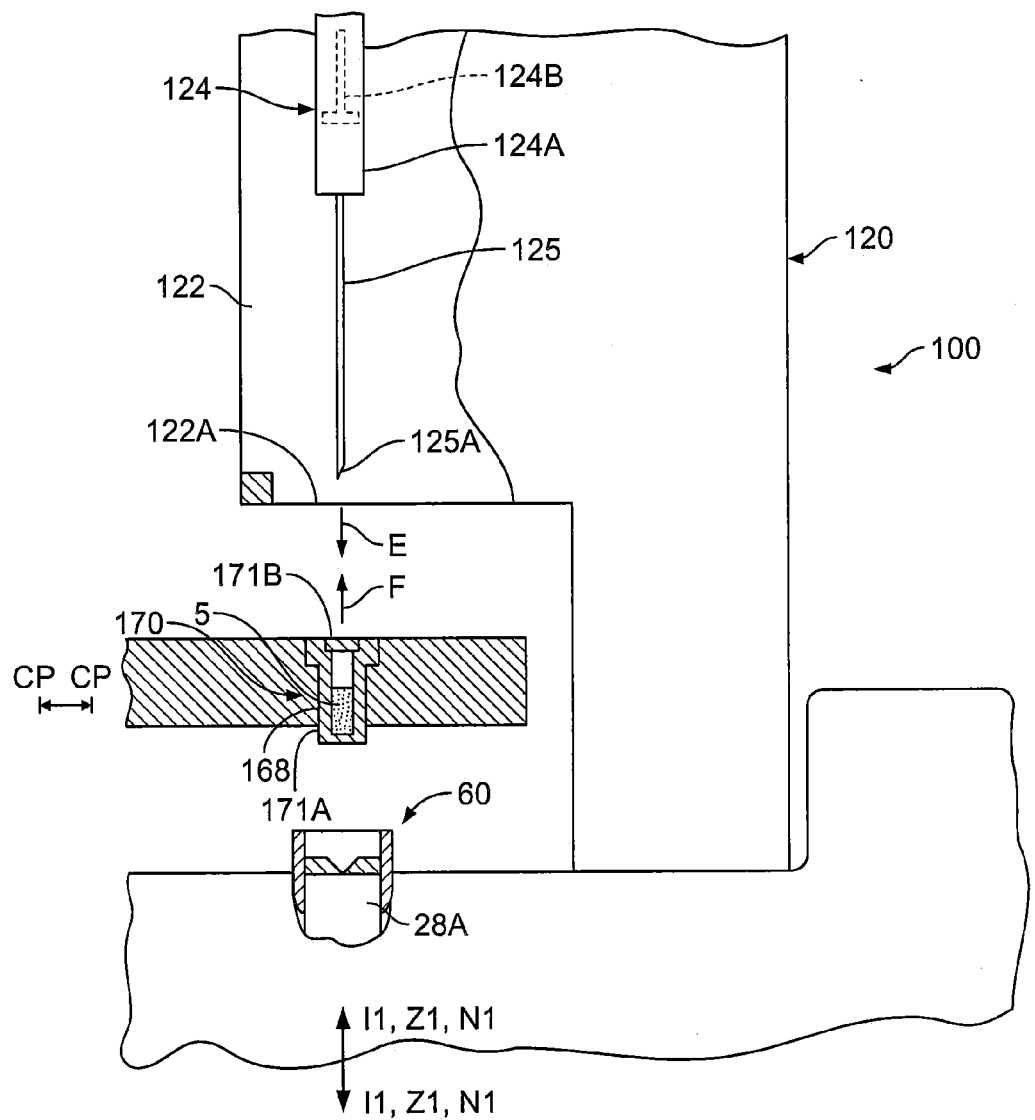
FIG. 4 is an enlarged, fragmentary, side elevational view of the GC system of FIG. 1, wherein a carousel tray of the autosampler is in position for sample extraction.
Figure 5:
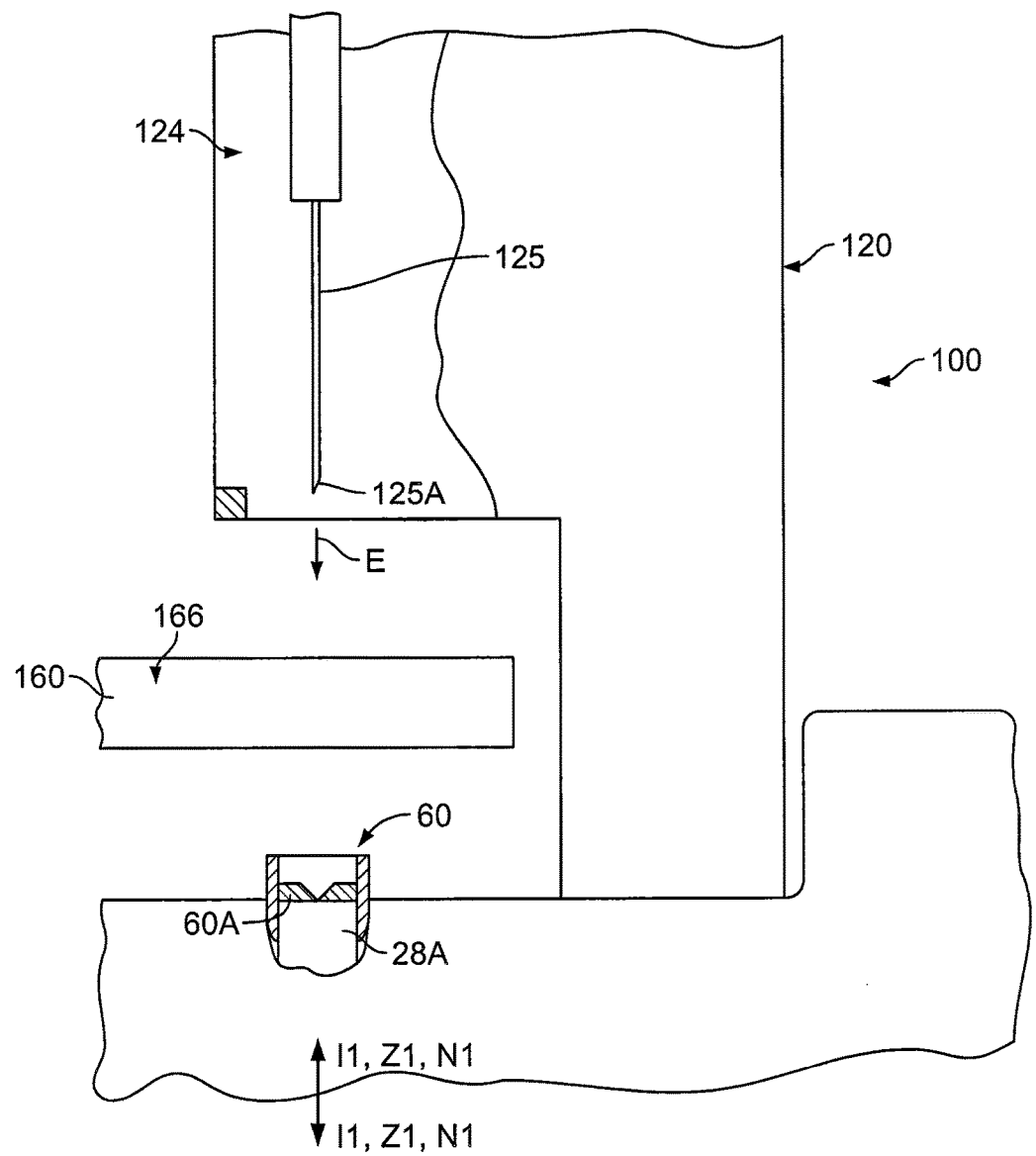
FIG. 5 is an enlarged, fragmentary, side elevational view of the GC system of FIG. 1, wherein the carousel tray is position for sample injection.

The sample slot array 169 includes a plurality of spatially distributed vial slots 168. The vials 170 are seated in the slots 168 and spatially distributed in a prescribed sample configuration or pattern H lying in a carousel plane CP-CP (FIG. 4). The carousel plane CP-CP may be substantially parallel to the injector port plane IP-IP.

As best seen in FIGS. 6-9, the vials 170 are arranged in four arcuate, concentric, circumferentially extending vial rows R1, R2, R3 and R4. Each row R1-R4 defines an arc concentric with the rotation axis P1-P1. The first row R1 is located a first distance D1 (FIG. 9) from the rotation axis P1-P1; the second row R2 is located a second distance D2 from the rotation axis P1-P1; the third row R3 is located a third distance D3 from the rotation axis P1-P1; and the fourth row R4 is located a fourth distance D4 from the rotation axis P1-P1. The distances D1-D4 decrease progressively from the first row R1 to the fourth row R4.

With reference to FIG. 4, each vial 170 includes a vial body 171A containing a sample supply 5. The sample supplies are samples including the sample analytes to be injected into the injectors 60, 62 for analysis. The vials 170 may also each include a cap or cover including a sealing member such as a diaphragm or septum 171B.

The carousel tray 160 is mounted on the carrier 140. More particularly, the carrier 140 fits within an opening 162A of the tray 160. The actuator 144 is operable (e.g., by the controller 50) to selectively rotate the tray 160 about a vertical (i.e., orthogonal to the plane CP-CP) rotation axis P1-P1 in a clockwise direction U and a counterclockwise direction V.

Figure 6:
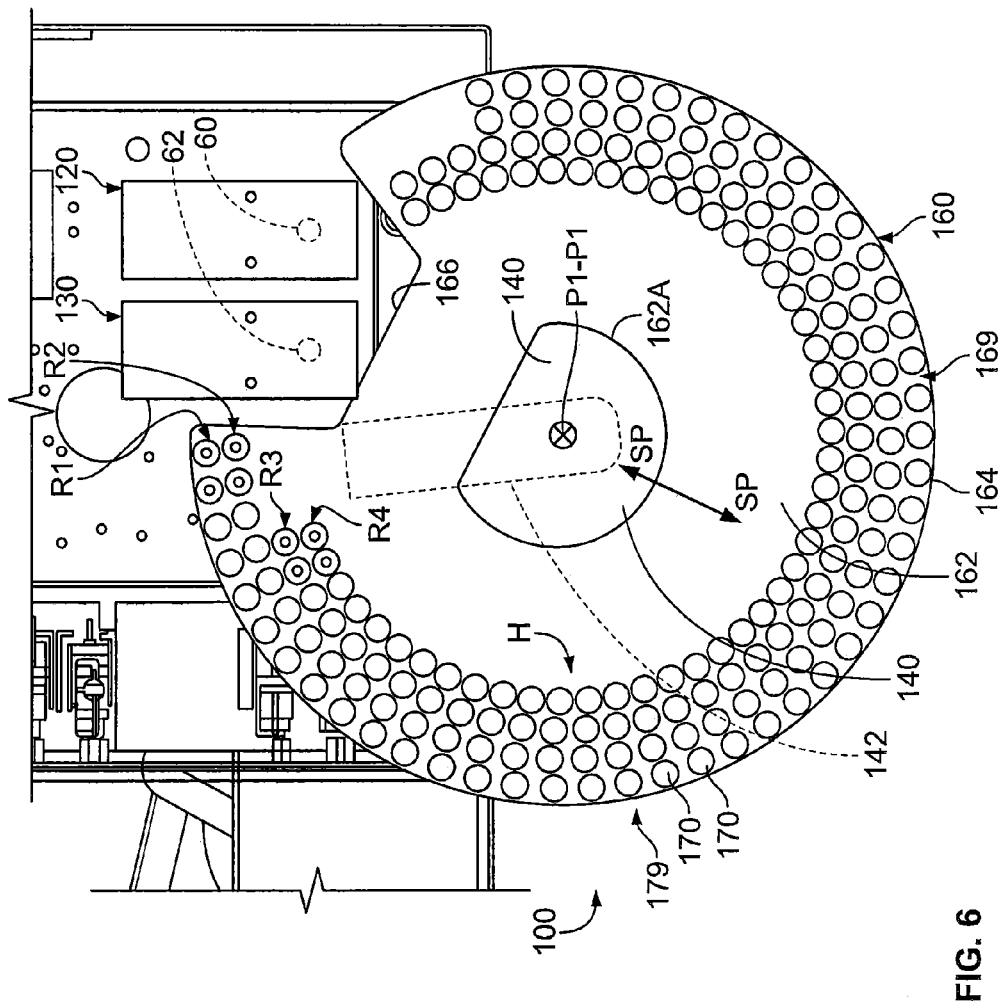
FIGS. 6-9 are fragmentary, top plan views of the GC system of FIG. 1 with the carousel in alternative positions.
Figure 7:
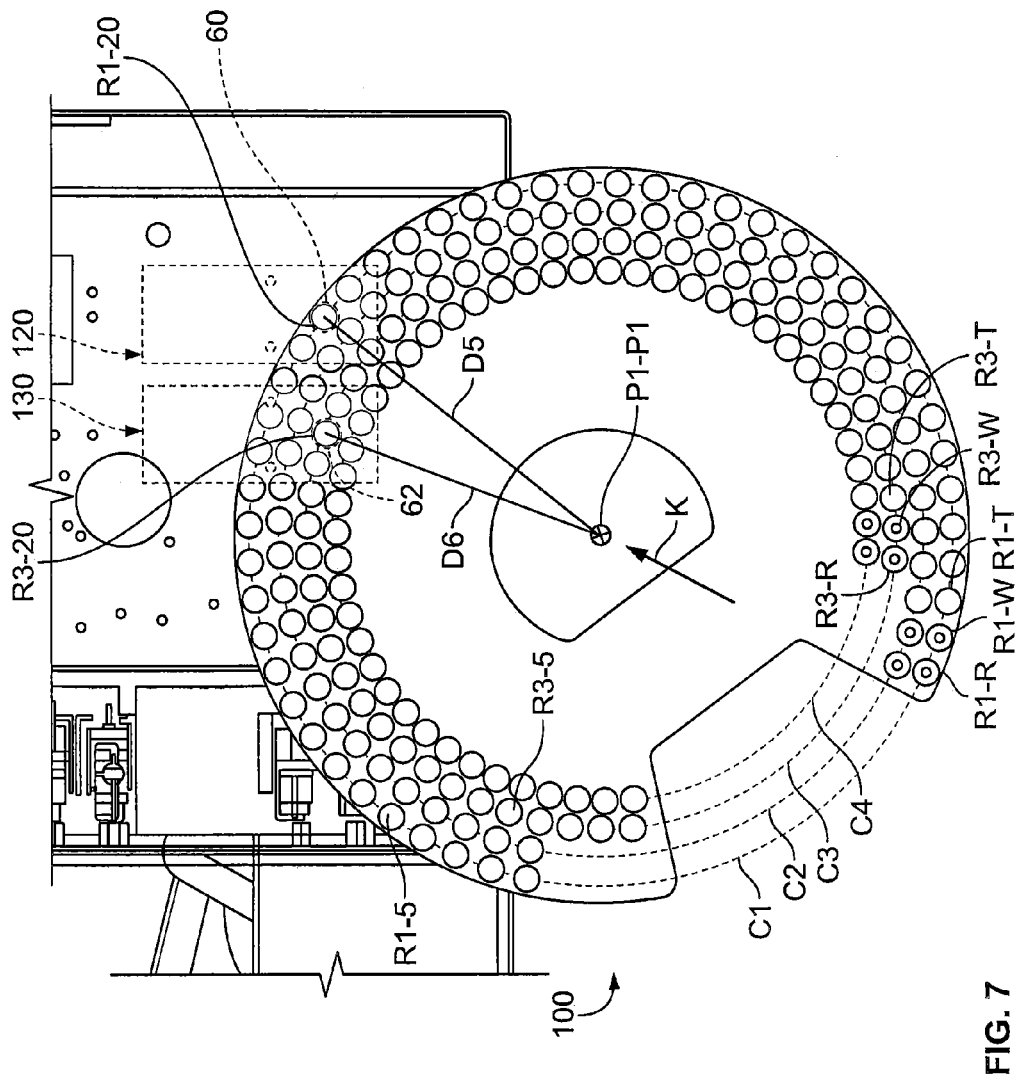
Figure 9:
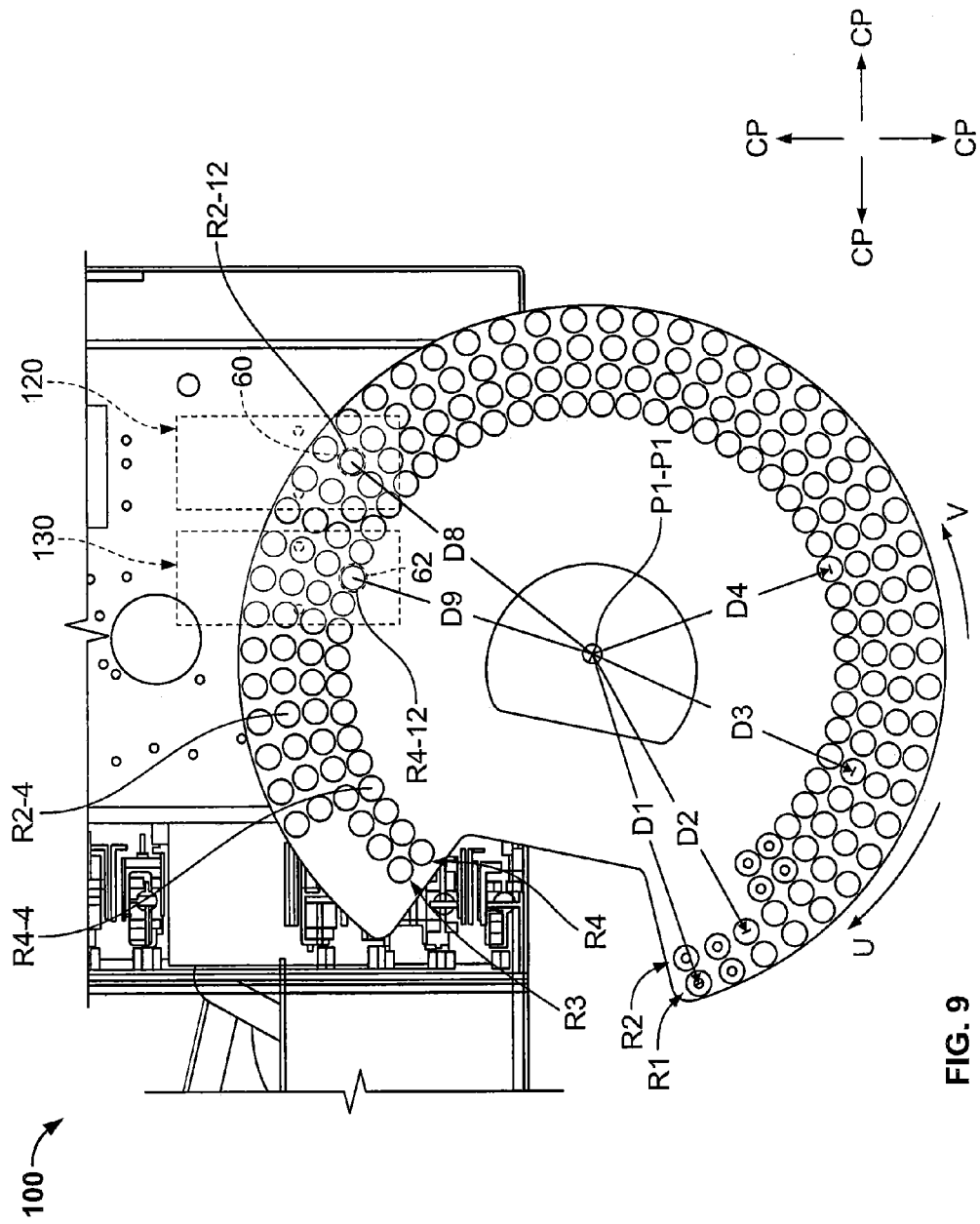

The carrier 140 is in turn mounted on the support arm 142. The support arm 142 is coupled to the cabinet 16 such that the support arm 142 (and thereby the tray 160) can be selectively translated by the actuator 146 through a short carousel shift path SP (FIG. 6). The carousel shift path SP may be linear or slightly arcuate. The path SP extends between a first tray lateral alignment position as shown in FIG. 7 and a second tray lateral alignment position as shown in FIG. 9. The actuator 146 can be controlled by the controller 50.

The autosampler 100 may be operated as follows in accordance with methods of the present technology. The controller 50 and the actuators 126, 136, 144, 146 collectively serve as a control system operative to execute the methods.

The autosampler 100 is affixed to the cabinet 16 such that first needle axis N1-N1 and the displacement axis Z1-Z1 are coaxially aligned with the first injector port axis I1-I1 and the second needle axis N2-N2 and the displacement axis Z2-Z2 are coaxially aligned with the second injector port axis I2-I2 as described above. The autosampler 100 may be mounted in the factory or thereafter (e.g., in the field or at customer lab or site). A mechanism or feature may be provided to enable adjustment of the positions of the syringes 124, 134 relative to the injectors 60, 62 to facilitate proper alignment.

The vials 170 containing the liquid samples 5 to be analyzed are mounted in their respective slots 168 in the carousel tray 160. The tray 160 is mounted on the carrier 140.

The controller 50 operates the actuators 144, 146 to position and reposition the tray 160, move the syringes 124, 134, and operate the syringes 124, 134 as described below. Generally described, the autosampler operates as follows to introduce selected samples 5 into the injectors 28A, 28B. First, the syringes 124, 134 are initially set or drawn upward along the axes Z1-Z1, Z2-Z2 so that the needle tips 125A, 135A are positioned higher than the tray assembly 161 as shown in FIG. 4. The tray 160 is then positioned such that two vials 170 containing the samples to be tested are located below the needle tips 125A, 135A (e.g., as shown in FIGS. 4 and 7). One of the selected vials 170 is interposed between the needle tip 125A and the injector port 60 on the axis I1-I1, and the other selected vial is interposed between the needle tip 135A and the injector port 62 on the axis I2-I2.

The needle 125 is then driven down in the direction E along the needle displacement axis Z1-Z1 to pierce the septum 171B and enter the vial on the axis I1-I1. Similarly, the needle 135 is driven down along the needle displacement axis Z2-Z2 to pierce the septum 171B and enter the vial lying on the axis I2-I2. The tips 125A, 135A may be positioned in the liquid of the sample or in the overlying headspaces of their corresponding vials. The plungers of the syringes 124, 134 are then retracted to draw or extract a selected quantity or aliquot of the each sample from each of the vials.

The needles 125, 135 of the syringes 124, 134 containing then extracted sample aliquots are then raised (in the direction F) along the axes Z1-Z1 and Z2-Z2, respectively, so that the needle tips 125A, 135A are again positioned higher than the tray assembly 161 (FIG. 4). The tray 169 is then rotated to the position of FIGS. 5 and 6 wherein the opening 166 is interposed between the needles 125, 135 and the injector ports 60, 62 (i.e., the axes and I2-I2 pass through the opening 166), providing clearance for the needles 125, 135 to access the injector ports 60, 62. With the tray 160 in this position, the needle 125 is driven down in the direction E along the needle displacement axis Z1-Z1 to pierce the septum 60A of the injector port 60 and enter the injector 28A on the axis I1-I1. Similarly, the needle 135 is driven down along the needle displacement axis Z2-Z2 to pierce the septum 60B of the injector port 60 and enter the injector 28B on the axis I2-I2.

With the needles 125, 135 in the injectors 28A, 28B, the syringes 124 and 134 are operated to dispense or inject the extracted aliquots therein into the injectors 28A and 28B, respectively. The extracted sample thus dispensed into the injector 28A is then processed by the GC subsystem 12 as described above. The aliquot thus dispensed into the injector 28B is processed by the GC subsystem 14 as described above.

According to some embodiments, the sample aliquots are dispensed by the syringes 124, 134 into their respective injector ports 60, 62 substantially simultaneously. According to some embodiments, the sample aliquots are dispensed by the syringes 124, 134 into their respective injector ports 60, 62 within less than 50 milliseconds of one another (i.e., the time between dispensation from the first of the needles 125, 135 and the other of the needles 125, 135 is less than 50 milliseconds).

According to some embodiments, the sample aliquots are extracted from the selected vials 170 by the syringes 124, 134 substantially simultaneously. According to some embodiments, the sample aliquots are extracted from the selected vials by the syringes 124, 134 within less than 50 milliseconds of one another.

Thus, the autosampler 100 can extract samples from two vials and dispense the samples into two fixed location (on X- and Y-axes) injector ports using two corresponding fixed location (on X- and Y-axes) syringes.

Additionally, the autosampler 100 can select and extract sample aliquots from a serially arranged plurality of vial pairs. For example, the vial rows R1 and R3 each include a series of vials 170 defining a circular track C1 and a circular track C3, respectively (FIG. 7). As discussed above, the rows R1 and R3 (i.e., the tracks C1 and C3) are located a radial distance D1 and D3 from the rotation axis P1-P1. With the tray 160 positioned as shown in FIG. 7 by the actuator 146 (the first lateral tray position), the needle axis N1-N1 is located a radial distance D5 from the rotation axis P1-P1 and the needle axis N2-N2 is located a radial distance D6 from the rotation axis P1-P1. The distance D5 is the same as the distance D1, the distance D6 is the same as the distance D3, and the distance D5 exceeds the distance D6 by an injector pair radial offset distance. Therefore, as the tray 160 is rotated about the rotation axis P1-P1, the needle axis N1-N1 follows (i.e., remains aligned with or in orthogonally intersecting relation with) the track C1. Likewise, as the tray 160 is rotated about the rotation axis P1-P1, the needle axis N2-N2 follows (i.e., remains aligned with or in orthogonally intersecting relation with) the track C3. That is, the needle axis N1-N1 follows the vials of the row R1 and the needle axis N2-N2 simultaneously follows the vials of the row R3.

In order to sample from a selected vial pair, the tray 160 is rotated about the rotation axis P1-P1 to index or position the selected vials 170 under and in coaxial alignment with the needles 125, 135 of the syringes 124, 134. As will be appreciated from FIGS. 6-9, the matched vials of each vial pair are circumferentially offset or staggered.

For example, in FIG. 7, the tray 160 is shown in a first rotational position wherein the syringe 124 is positioned over the vial R1-20 (at row R1, sequential position or slot 20) and the syringe 134 is positioned over the vial R3-20 (at row R3, sequential position or slot 20). The autosampler 100 can then extract quantities of the samples from the vials R1-20, R3-20 and simultaneously dispense the extracted samples into the injector ports 60, 62 as described above.

Figure 8:
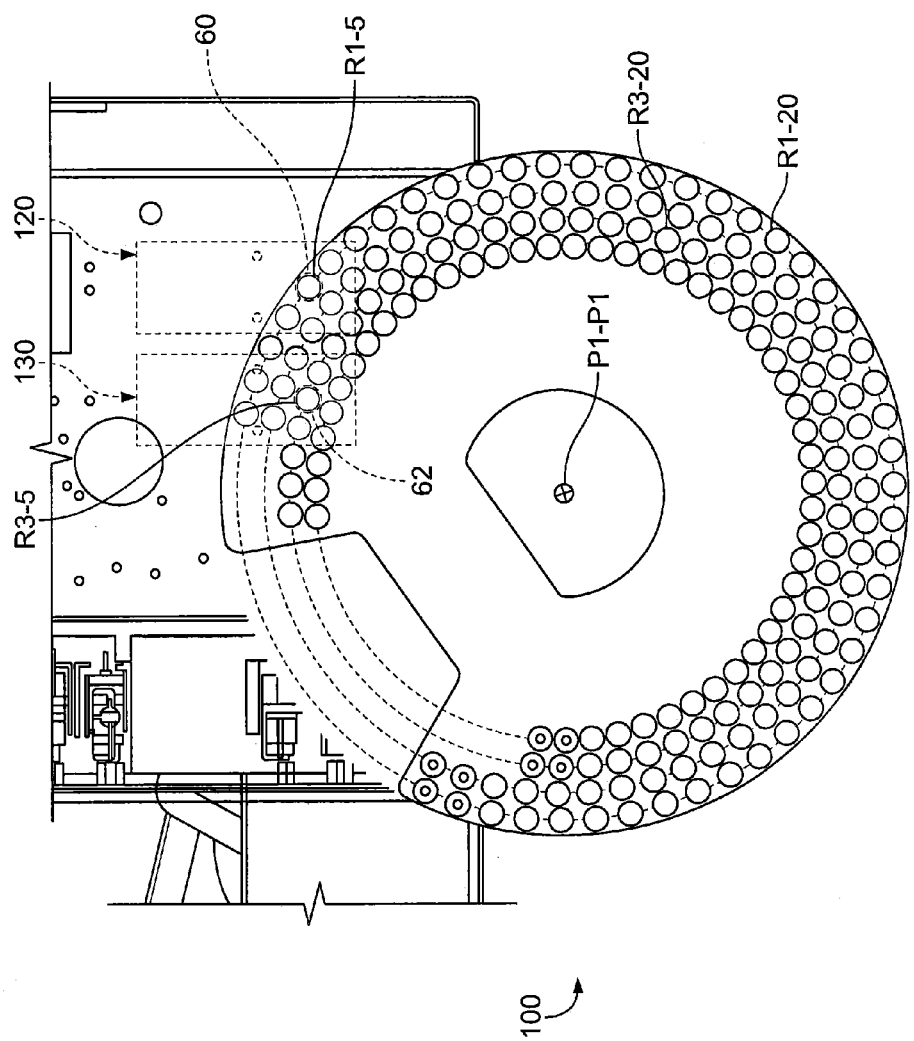

By way of further example, the tray 160 can be rotated to a second rotational position as shown in FIG. 8 wherein the syringe 124 is positioned over the vial R1-5 (at row R1, sequential position or slot 5) and the syringe 134 is simultaneously positioned over the vial R3-5 (at row R3, sequential position or slot 5). The autosampler 100 can then extract quantities of the samples from the vials R1-5, R3-5 and simultaneously dispense the extracted samples into the injector ports 60, 62 as described above.

The tray 160 may also be rotated to: a further rotational position wherein the syringes 124 and 134 are simultaneously positioned over and draw from vials R1-W and R3-W, respectively, which contain wash fluid; a further rotational position wherein the syringes 124 and 134 are positioned over and draw from vials R1-R and R3-R, respectively, which contain rinse fluid; and a further rotational position wherein the syringes 124 and 134 are positioned over and dispense into vials R1-T and R3-T, respectively, which serve as waste receptacles. These positions and vials may be used in suitable sequence to wash, rinse and empty the syringes 124, 134 for further use.

The autosampler 100 can also select and extract sample aliquots from a second pair of rows R2, R4 of serially arranged vials. The vial rows R2 and R4 each include a series of vials 170 defining a circular track C2 and a circular track C4, respectively (FIG. 7). As discussed above, the rows R2 and R4 (i.e., the tracks C2 and C4) are located radial distances D2 and D4 from the rotation axis P1-P1.

In order to select from the rows R2, R4, the tray 160 is translated in the direction K by the actuator 146 and thereby repositioned as shown in FIG. 9 to the second tray lateral position. In the second tray lateral position, the needle axis N1-N1 is located a radial distance D8 from the rotation axis P1-P1 and the needle axis N2-N2 is located a radial distance D9 from the rotation axis P1-P1. The distance D8 is the same as the distance D2, the distance D9 is the same as the distance D4, and the distance D8 exceeds the distance D9 by an injector pair radial offset distance. Therefore, as the tray 160 is rotated about the rotation axis P1-P1, the needle axis N1-N1 follows (i.e., remains aligned with or in orthogonally intersecting relation with) the track C2. Likewise, as the tray 160 is rotated about the rotation axis P1-P1, the needle axis N2-N2 follows (i.e., remains aligned with or in orthogonally intersecting relation with) the track C4. That is, the needle axis N1-N1 follows the vials of the row R2 and the needle axis N2-N2 follows the vials of the row R4.

In order to sample from a selected vial pair, the tray 160 is rotated about the rotation axis P1-P1 to index or position the selected vials 170 of the rows R2, R4 under and in coaxial alignment with the needles 125, 135 of the syringes 124, 134 as described above with reference to the rows R1, R2.

For example, in FIG. 9, the tray 160 is shown in a first rotational position wherein the syringe 124 is positioned over the vial R2-12 (at row R2, sequential position or slot 12) and the syringe 134 is simultaneously positioned over the vial R4-12 (at row R4, sequential position or slot 12). The autosampler 100 can then extract quantities of the samples from the vials R2-12, R4-12 and simultaneously dispense the extracted samples into the injector ports 60, 62 as described above. By way of further example, the tray 160 can be rotated to a second rotational position wherein the syringe 124 is positioned over the vial R2-4 (at row R2, sequential position or slot 4) and the syringe 134 is simultaneously positioned over the vial R4-4 (at row R4, sequential position or slot 4). The autosampler 100 can then extract quantities of the samples from the vials R2-4, R4-4 and simultaneously dispense the extracted samples into the injector ports 60, 62 as described above.

According to some embodiments, the towers 120 and 130 are fixed in alignment with the injector ports 60 and 62, respectively, throughout and between the steps of drawing the samples from the respective vials and injecting the samples in the respective injector ports 60, 62 (i.e., the axis N1-N1 remains in fixed alignment with the axis I1-I1, and the axis N2-N2 remains in fixed alignment with the axis I2-I2). According to some embodiments, the towers 120, 130 and the injector ports 60, 62 are all stationary with respect to the deck 16B throughout and between these steps.

Thus, the autosampler 100 can be operated to simultaneously extract aliquots from selected pairs of matched vials 170 in the rows R1 and R3 by moving the tray 160 to the first lateral position and, alternatively, to simultaneously extract aliquots from selected pairs of matched vials 170 in the rows R2 and R4 by moving the tray 160 to the second lateral position. The extracted aliquots, from either pair of rows R1, R3 or R2, R4 can then be simultaneously dispensed into the injector ports 60, 62. Thus, the autosampler 100 can enable dual parallel withdrawal and injection of selected samples.

According to some embodiments, the tray 160 includes at least two circumferentially extending rows of vials and each row is aligned with a respective syringe 124, 134. According to some embodiments, the tray 160 includes at least four circumferentially extending rows of vials, two of the rows are alternatively positionable in alignment with the syringe 124, and two of the rows are alternatively positionable in alignment with the syringe 134 as described above and shown in FIGS. 6-9. According to some embodiments, the tray 160 includes at least 10 vials 170 or vial slots 168 in each row and, in some embodiments, in the range of from about 20 to 100 vials 170 or vial slots 168.

The towers 120, 130 may include any suitable sample transfer apparatus. Suitable apparatus for the towers 120, 130 may include the PAL BLI injector available from CTC Analytics AG of Switzerland, for example.

The actuators 144, 146, 126, 136 may be any suitable devices capable of executing the described functions. In some embodiments, the actuators 144, 146, 126, 136 include electric motors, solenoids, linear actuators, and/or hydraulic actuators. Each of the actuators 144, 146, 126, 136 may include two or more actuators. The apparatus may be configured such that a single actuator serves as two or more of the actuators 144, 146, 126, 136.

Operations described herein can be executed by or through the controller 50. The actuators 144, 146, 126, 136 and other devices of the system 10 can be electronically controlled. According to some embodiments, the controller 50 programmatically executes some, and in some embodiments all, of the steps described. According to some embodiments, the movements of the actuators 144, 146, 126, 136 are fully automatically and programmatically executed by the controller 50.

Embodiments of the controller 50 logic may take the form of an entirely software embodiment or an embodiment combining software and hardware aspects, all generally referred to herein as a "circuit" or "module." In some embodiments, the circuits include both software and hardware and the software is configured to work with specific hardware with known physical attributes and/or configurations. Furthermore, controller 30 logic may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or other storage devices.

Figure 11:
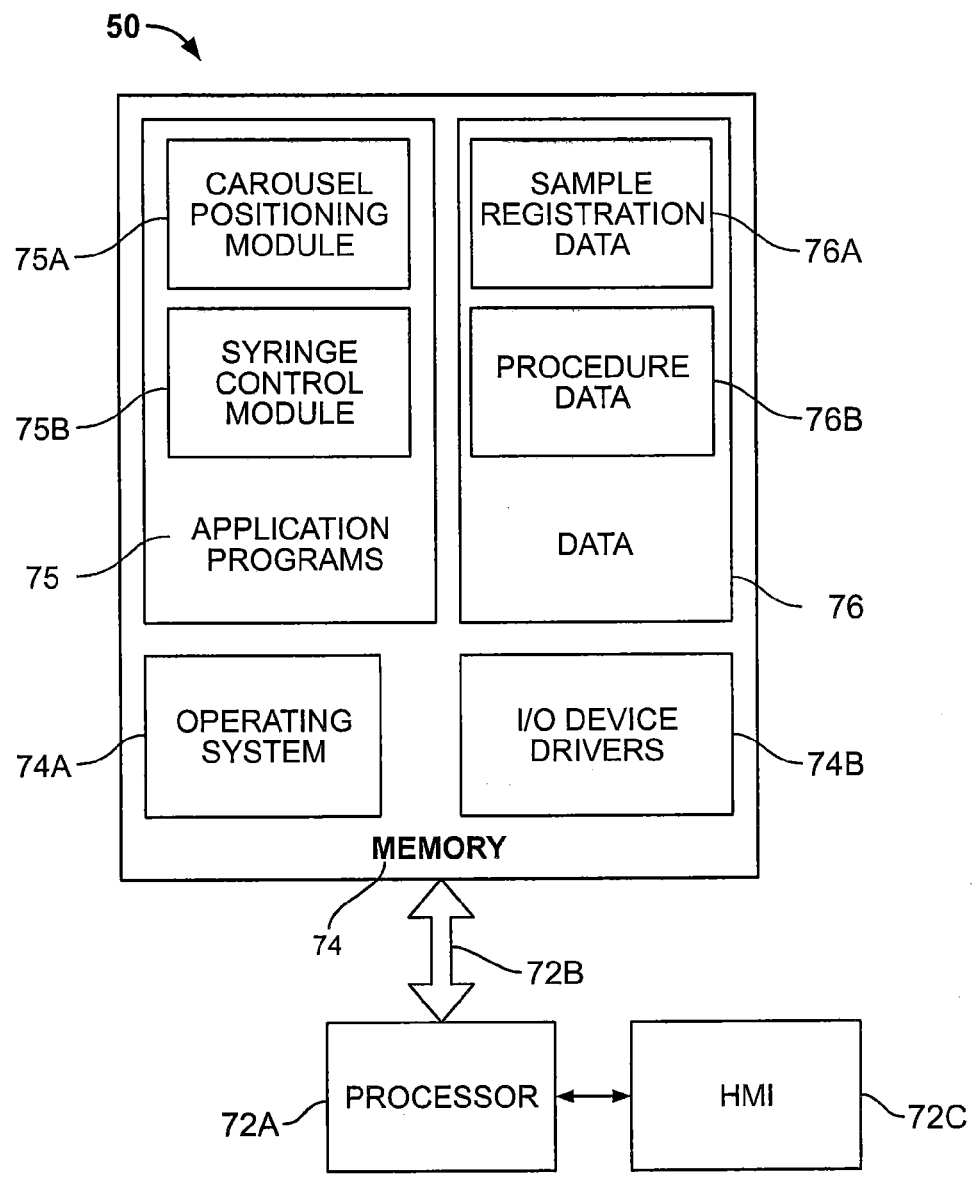
FIG. 11 is a schematic diagram representing a controller forming a part of the GC system of FIG. 1.

FIG. 11 is a schematic illustration of a circuit or data processing system that can be used in the controller 50. The circuits and/or data processing systems may be incorporated in a digital signal processor 72 in any suitable device or devices. The processor 72A communicates with the HMI 72C and memory 74 via an address/data bus 72B. The processor 72A can be any commercially available or custom microprocessor. The memory 74 is representative of the overall hierarchy of memory devices containing the software and data used to implement the functionality of the data processing system. The memory 74 can include, but is not limited to, the following types of devices: cache, ROM, PROM, EPROM, EEPROM, flash memory, SRAM, and DRAM.

FIG. 11 illustrates that the memory 74 may include several categories of software and data used in the data processing system: the operating system 74A; the application programs 75; the input/output (I/O) device drivers 74B; and data 76. The data 76 can include equipment-specific data. FIG. 11 also illustrates that the data 76 can include sample registration data 76A, and procedure data 76B. FIG. 11 also illustrates that application programs 75 can include a carousel positioning module 75A and a syringe control module 75B. The sample registration data 76A can include data representing characteristics of the sample supplies 5 contained in the respective vials 170. The procedure data 76B can include data representing a protocol or sequence of steps to execute the procedures described herein. The carousel positioning module 75A can be used to control the actuators 144, 146 to position and reposition the carousel tray 160 relative to the needles 125, 135 and the injector ports 60, 62. The syringe control module 75B can be used to control actuation of the actuators 126, 136 raise and lower the needles 125, 135 and to draw the samples from the vials 170 and dispense the samples into the injector ports 60, 62.

As will be appreciated by those of skill in the art, the operating system 74A may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 74B typically include software routines accessed through the operating system 74A by the application programs 75 to communicate with devices such as I/O data port(s), data storage and certain memory components. The application programs 75 are illustrative of the programs that implement the various features of the data processing system and can include at least one application, which supports operations according to embodiments of the present technology. Finally, the data 76 represents the static and dynamic data used by the application programs 75, the operating system 74A, the I/O device drivers 34C, and other software programs that may reside in the memory 74.

As will be appreciated by those of skill in the art, other configurations may also be utilized while still benefiting from the teachings of the present technology. For example, one or more of the modules may be incorporated into the operating system, the I/O device drivers or other such logical division of the data processing system. Thus, the present technology should not be construed as limited to the configuration of FIG. 11, which is intended to encompass any configuration capable of carrying out the operations described herein. Further, one or more of the modules can communicate with or be incorporated totally or partially in other components, such as the controller 50.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A gas chromatography system comprising:
   at least one gas chromatography subsystem including a first injector port and a second injector port;
   an autosampler including:
      a carousel tray mounted for rotation about a rotation axis, wherein the carousel tray is mounted above the first and second injector ports, and wherein the carousel tray includes:
         an arcuately extending first row of sample reservoirs; and
         an arcuately extending second row of sample reservoirs;
      a first sample transfer tower to extract samples from the first row of sample reservoirs;
      a second sample transfer tower to extract samples from the second row of sample reservoirs; and
      a control system operative to:
         selectively position the carousel tray relative to the first and second sample transfer towers to align the first sample transfer tower with a first sample reservoir in the first row and to align the second sample transfer tower with a second sample reservoir in the second row;
         simultaneously draw a first sample from the first sample reservoir using the first sample transfer tower and a second sample from the second sample reservoir using the second sample transfer tower; and sequentially thereafter simultaneously inject the first sample into the first injector port using the first sample transfer tower and the second sample into the second injector port using the second sample transfer tower.

2. The gas chromatography system of claim 1 including first and second gas chromatography subsystems each including:
a sample injector;
a column fluidly connected to the sample injector; and
a detector fluidly connected to the column;
wherein the sample injector of the first gas chromatography subsystem includes the first injector port and the sample injector of the second gas chromatography subsystem includes the second injector port.

3. The gas chromatography system of claim 1 wherein the control system is operative to draw the first and second samples from the selected pair of the first and second sample reservoirs using the first and second sample transfer towers within less than 50 milliseconds of one another.

4. The gas chromatography system of claim 1 wherein the control system is operative to inject the first and second samples into the first and second injector ports using the first and second sample transfer towers within less than 50 milliseconds of one another.

5. The gas chromatography system of claim 1 wherein the control system is operative to:
selectively reposition the carousel tray relative to the first and second sample transfer towers to align the first and second sample transfer towers with a third sample reservoir in the first row and a fourth sample reservoir in the second row, respectively;
simultaneously draw a third sample from the third sample reservoir using the first sample transfer tower and a fourth sample from the fourth sample reservoir using the second sample transfer tower; and sequentially thereafter
simultaneously inject the third sample into the first injector port using the first sample transfer tower and the fourth sample into the second injector port using the second sample transfer tower.

6. The gas chromatography system of claim 1 wherein the first and second sample transfer towers are fixed in alignment with the first and second injector ports, respectively.

7. The gas chromatography system of claim 1 wherein:
each of the first and second sample transfer towers includes:
a syringe including a needle; and
a syringe actuator; and
the control system is operative to:
drive the needles of the first and second sample transfer towers into the first and second sample reservoirs and to operate the syringes using the associated syringe actuators to draw the first and second samples therefrom; and
drive the needles of the first and second sample transfer towers into the first and second injector ports and to operate the syringes using the associated syringe actuators to inject the first and second samples into the first and second injector ports.

8. The gas chromatography system of claim 7 wherein:
the needle of the first sample transfer tower has a first needle axis;
the needle of the second sample transfer tower has a second needle axis;
the first injector port is aligned with the first needle axis and the second injector port is aligned with the second needle axis; and the autosampler is configured to position the carousel between the first and second injector ports and the needles of the first and second transfer towers such that a sample reservoir in the first row is aligned with the first needle axis and a sample reservoir in the second row is aligned with the second needle axis.

9. The gas chromatography system of claim 1 wherein the second row is located radially between the first row and the rotation axis of the carousel tray.

10. A method for performing gas chromatography, the method comprising:
providing a gas chromatography system including:
at least one gas chromatography subsystem including a first injector port and a second injector port;
an autosampler including:
a carousel tray mounted for rotation about a rotation axis, wherein the carousel tray is mounted above the first and second injector ports, and wherein the carousel tray includes:
an arcuately extending first row of sample reservoirs; and
an arcuately extending second row of sample reservoirs;
a first sample transfer tower to extract samples from the first row of sample reservoirs;
a second sample transfer tower to extract samples from the second row of sample reservoirs; and
a control system;
selectively positioning the carousel tray relative to the first and second sample transfer towers to align the first sample transfer tower with a first sample reservoir in the first row and to align the second sample transfer tower with a second sample reservoir in the second row;
simultaneously drawing a first sample from the first sample reservoir using the first sample transfer tower and a second sample from the second sample reservoir using the second sample transfer tower; and sequentially thereafter
simultaneously injecting the first sample into the first injector port using the first sample transfer tower and the second sample into the second injector port using the second sample transfer tower.

11. The method of claim 10 wherein:
the gas chromatography system includes first and second gas chromatography subsystems each including:
a sample injector;
a column fluidly connected to the sample injector; and
a detector fluidly connected to the column;
wherein the sample injector of the first gas chromatography subsystem includes the first injector port and the sample injector of the second gas chromatography subsystem includes the second injector port.

12. The method of claim 10 including drawing the first and second samples from the first and second sample reservoirs using the first and second sample transfer towers within less than 50 milliseconds of one another.

13. The method of claim 10 including injecting the first and second samples into the first and second injector ports using the first and second sample transfer towers within less than 50 milliseconds of one another.

14. The method of claim 10 including:
selectively repositioning the carousel tray relative to the first and second sample transfer towers to align the first and second sample transfer towers with a third sample reservoir in the first row and a fourth sample reservoir in the second row, respectively;

simultaneously drawing a third sample from the third sample reservoir using the first sample transfer tower and a fourth sample from the fourth sample reservoir using the second sample transfer tower; and sequentially thereafter simultaneously injecting the third sample into the first injector port using the first sample transfer tower and the fourth sample into the second injector port using the second sample transfer tower.

15. The method of claim 10 wherein the first and second sample transfer towers are fixed in alignment with the first and second injector ports, respectively, throughout the steps of:

simultaneously drawing the first sample from the first sample reservoir using the first sample transfer tower and the second sample from the second sample reservoir using the second sample transfer tower; and simultaneously injecting the first sample into the first injector port using the first sample transfer tower and the second sample into the second injector port using the second sample transfer tower.

16. The method of claim 10 wherein:

each of the first and second sample transfer towers includes:
a syringe including a needle; and
a syringe actuator; and the method includes:
driving the needles of the first and second sample transfer towers into the first and second sample reservoirs and operating the syringes using the associated syringe actuators to draw the first and second samples therefrom; and
driving the needles of the first and second sample transfer towers into the first and second injector ports and operating the syringes using the associated syringe actuators to inject the first and second samples into the first and second injector ports.

17. The method of claim 16 wherein:

the needle of the first sample transfer tower has a first needle axis;

the needle of the second sample transfer tower has a second needle axis;

the first injector port is aligned with the first needle axis and the second injector port is aligned with the second needle axis; and the step of selectively positioning the carousel tray relative to the first and second sample transfer towers includes positioning the carousel between the first and second injector ports and the needles of the first and second transfer towers such that a sample reservoir in the first row is aligned with the first needle axis and a sample reservoir in the second row is aligned with the second needle axis.

18. The method of claim 10 wherein the second row is located radially between the first row and the rotation axis of the carousel tray.

* * * * *

UNITED STATES PATENT AND TRADEMARK OFFICE
CERTIFICATE OF CORRECTION

PATENT NO. : 9,810,668 B2
APPLICATION NO. : 14/626222
DATED : November 7, 2017
INVENTOR(S) : Timothy Neal Page 1 of 1

It is certified that error appears in the above-identified patent and that said Letters Patent is hereby corrected as shown below:

In the Specification

Column 2, Line 42: Please correct "tray," to read -- tray. --

Column 10, Line 13: Please correct "the axes and" to read -- the axes I1-I1 and --

In the Claims

Column 15, Claim 3, Line 17: Please correct "samples from the selected pair of the first" to read -- samples from the first --

Signed and Sealed this
Fourteenth Day of August, 2018

Andrei Iancu
*Director of the United States Patent and Trademark Office*